United States Patent [19]
Hansen, Jr. et al.

[11] Patent Number: 6,136,829
[45] Date of Patent: Oct. 24, 2000

[54] OXATHIADIAZOLE DERIVATIVES USFUL AS INOS INHIBITORS

[75] Inventors: Donald W. Hansen, Jr., Skokie; Ariia A. Bergmanis, Des Plaines; Timothy J. Hagen, Gurnee; E. Ann Hallinan, Evanston; Steven W. Kramer, Des Plaines, all of Ill.; Suzanne Metz, Chesterfield, Mo.; Karen B. Peterson, Vernon Hills; Barnett S. Pitzele, Skokie, both of Ill.; Foe S. Tjoeng, Manchester; Mihaly V. Toth, St. Louis, both of Mo.; Mahima Trivedi, Glenview, Ill.; R. Keith Webber, St. Peters, Mo.; Sofya Tsymbalov, Des Plaines; Rolando E. Gapud, Chicago, both of Ill.

[73] Assignee: G.D. Searle & Co., Chicago, Ill.

[21] Appl. No.: 09/356,735

[22] Filed: Jul. 19, 1999

Related U.S. Application Data

[62] Division of application No. 08/898,110, Jul. 22, 1997, Pat. No. 5,981,556.

[51] Int. Cl.⁷ .......................... C07D 291/04; A61K 31/41
[52] U.S. Cl. ............................. 514/360; 548/122
[58] Field of Search ................................... 548/122, 123, 548/124; 514/360

[56] References Cited

U.S. PATENT DOCUMENTS

| | | |
|---|---|---|
| 2,049,582 | 8/1936 | Ziegler . |
| 3,109,848 | 11/1963 | Bortnick et al. . |
| 3,121,093 | 2/1964 | Bortnick et al. . |
| 3,132,151 | 5/1964 | Bortnick et al. . |
| 3,501,487 | 3/1970 | Poos . |
| 3,563,994 | 2/1971 | Wollweber et al. . |
| 3,694,432 | 9/1972 | Hershenson . |
| 3,725,435 | 4/1973 | Poos . |
| 3,816,457 | 6/1974 | Grisar et al. . |
| 4,046,909 | 9/1977 | Rasmussen et al. . |
| 4,061,746 | 12/1977 | Blohm et al. . |
| 4,126,613 | 11/1978 | Grisar et al. . |
| 4,126,621 | 11/1978 | Grisar et al. . |
| 4,153,235 | 5/1979 | Grisar et al. . |
| 4,443,468 | 4/1984 | Maillard et al. . |
| 4,523,020 | 6/1985 | Moormann et al. . |
| 4,525,476 | 6/1985 | Butler et al. . |
| 4,533,739 | 8/1985 | Pitzele et al. . |
| 4,556,674 | 12/1985 | Maillard et al. . |
| 4,579,951 | 4/1986 | Pitzele et al. . |
| 4,699,918 | 10/1987 | Maillard et al. . |
| 4,855,444 | 8/1989 | Wambach . |
| 4,962,204 | 10/1990 | Wambach . |
| 5,015,633 | 5/1991 | Sudilovsky . |
| 5,028,627 | 7/1991 | Kilbourn et al. . |
| 5,051,444 | 9/1991 | Tamoto et al. . |
| 5,059,712 | 10/1991 | Griffith . |
| 5,081,148 | 1/1992 | Braquet et al. . |
| 5,132,453 | 7/1992 | Griffith . |
| 5,196,439 | 3/1993 | Sugimoto et al. . |
| 5,216,025 | 6/1993 | Gross et al. . |
| 5,246,971 | 9/1993 | Williamson et al. . |
| 5,266,594 | 11/1993 | Dawson et al. . |
| 5,273,875 | 12/1993 | Griffith . |
| 5,621,004 | 4/1997 | Dunn et al. . |
| 5,629,322 | 5/1997 | Guthikonda et al. . |

FOREIGN PATENT DOCUMENTS

| | | |
|---|---|---|
| 191584 | 10/1978 | Czech Rep. . |
| 0370320 | 5/1990 | European Pat. Off. . |
| 0446699 | 9/1991 | European Pat. Off. . |
| 0462948 | 12/1991 | European Pat. Off. . |
| 0676196 | 10/1995 | European Pat. Off. . |
| 0713704 | 5/1996 | European Pat. Off. . |
| 0713876 | 5/1996 | European Pat. Off. . |
| 0717040 | 6/1996 | European Pat. Off. . |
| 1180876 | 2/1970 | United Kingdom . |
| 1367598 | 9/1974 | United Kingdom . |
| 2240041 | 7/1991 | United Kingdom . |
| 91/04023 | 4/1991 | WIPO . |
| 91/04024 | 4/1991 | WIPO . |
| 93/13055 | 7/1993 | WIPO . |
| 93/16721 | 9/1993 | WIPO . |
| 93/24126 | 12/1993 | WIPO . |
| 94/12163 | 6/1994 | WIPO . |
| 94/12165 | 6/1994 | WIPO . |
| 94/14780 | 7/1994 | WIPO . |
| 94/16729 | 8/1994 | WIPO . |
| 95/05363 | 2/1995 | WIPO . |
| 95/11231 | 4/1995 | WIPO . |
| 95/31987 | 11/1995 | WIPO . |
| 95/32203 | 11/1995 | WIPO . |
| 96/14842 | 5/1996 | WIPO . |
| 96/14844 | 5/1996 | WIPO . |
| 96/18616 | 6/1996 | WIPO . |
| 97/16430 | 5/1997 | WIPO . |

OTHER PUBLICATIONS

Perrin et al., "Absence of Stereoelectronic Control in Hydrolysis of Cyclic Amidines", *J. Am. Chem. Soc.*, vol. 108, No. 19, pp. 5997–6003, 1986.

Huber et al., "Saturated Heterocycles, Part 88. Synthesis of a New Ring System: Dipyrido–[1.2–a:4,3–d] pyrimidin–11–one Derivatives", *J. Chem. Soc. Perkin Trans. 1*, pp. 909–912, 1987.

Kökösi et al., "Nitrogen Bridgehead Compounds. Part 19(1). Synthesis of Polymethylenepyrimidin–4–ones", *J. Heterocyclic Chem.*, vol. 19, pp. 909–912, 1982.

Brown et al., Hydropyrimidines, Part II, pp. 4041–4045, 1962.

Adcock et al., 2–Amino–2–imidazolines 2–Amino–2–oxazolines, Part II, pp. 474–479, 1965.

Stefanye et al., "Cyclic Guanidines from Nitrimino Compounds", *J. Am. Chem. Soc.*, vol. 77, No. 3, pp. 761–762, 1955.

Klayman et al., "2–Amino–2–thiazoline. VII. Unequivocal Structure Assignment of the Products of the Reaction of 2–Amino–2–thiazoline and Its Analogs with Carbethoxy Isothiocyanate", *J. Org. Chem.*, vol. 39, No. 13, pp. 1819–1823, 1974.

(List continued on next page.)

*Primary Examiner*—Robert Gerstl
*Attorney, Agent, or Firm*—Alan L. Scrivner

[57] ABSTRACT

1,3-diazolino and 1,3-diazolidino heterocycle derivatives useful as nitric oxide synthase inhibitors.

10 Claims, No Drawings

OTHER PUBLICATIONS

Moriconi et al., "Synthesis and Reactions of Cyclic Amidines", *J. Org. Chem.*, vol. 33, No. 5, pp. 2109–2111, 1968.

Wagenaar et al., "Methodology for the Preparation of N–Guanidino–Modified Arginines and Related Derivatives", *J. Org. Chem.*, vol. 58, No. 1, pp. 4331–4338, 1993.

Gutteridge, "Acylation of 2–Amino–5,5–dimethyl–Δ–pyrroline 1–Oxide", *J. Chem. Soc.*, (C), pp. 3121–3125, 1971.

Langlois et al., "Derivatives of Imidazole, 1,3,4–triazole and tetrazole", *J. Heterocycl. Chem.*, vol. 19, No. 1, pp. 193–200, 1982 (English Summary, p. 200).

Langolis et al., "Synthesis and Antidepressant Properties of 2–Amino–4–phenyl–1–pyrroline Derivatives", *Eur. J. Med. Chem.*, vol. 13, No. 2, pp. 161–169, 1978 (English Summary, p. 169).

Klötzer et al. "Acylderivatives of 2–Amino–1–pyrrolines", *Monatshefte für Chemie*, vol. 102, No. 2, pp. 627–634, 1971 (English Summary, p. 627).

Klötzer et al. "Synthesis of Substituted 2–Amino–1–pyrrolines, I." *Monatshefte für Chemie*, vol. 101, No. 5, pp. 1263–1270, 1970 (English Summary, p. 1263).

Nakane et al., "Novel Potent and Selective Inhibitors of Inducible Nitric Oxide Synthase", *Molecular Pharmacology*, vol. 47, pp. 831–834, 1995.

Dunbar et al., "Design, Synthesis, and Neurochemical Evaluation of 2–Amino–5–(alkoxycarbonyl)–3,4,5,6–tetrahydopyridines and 2–Amino–5–(alkoxycarbonyl)–1,4,5,6–tetrahydropyrimidines as $M_1$ Muscarinic Receptor Agonists", *J. Med. Chem.*, vol. 37, No. 17, pp. 2774–2782, 1994.

Klötzer et al., "Synthesis of Substituted 2–Aminopyrrolines, II." *Monatshefte für Chemie*, vol. 101, No. 6, pp. 1841–1850, 1970 (English Summary, p. 1841).

Berge et al., "Pharmaceutical Salts", *J. Pharm. Sci.*, vol. 66, No. 1, pp. 1–19, 1977.

Moncada et al., "Nitric Oxide: Physiology, Pathophysiology, and Pharmacology", *Pharmacological Reviews*, Vo. 43, No. 2, pp. 109–142, 1991.

Moncada et al, "Biosynthesis of Nitric Oxide from L–Arginine", *Biochemical Pharm.*, vol 38, No. 11, pp. 1709–1715, 1989.

Mazurek et al., "Theoretical Studies of Tautomerism of Clonidine Vacuum and in Water Medium", *Theochem*, 82(1–2), 23–8, 1991.

Bertolini et al., "Nitric Oxide Synthase Inhibitors: Recent Advances", *Cardiovascular & Renal Patent Update*, Ashley Publications Ltd., pp. 1339–1345, 1994.

Culvenor, C.C.J. et al, *Aust. J. Chem.*, 24(1971) 371–375.

Caujolle, R. et al., *Eur. J. Med. Chem. Chim. Ther.*, 28(1) (1993) 29–35.

Kato et al, *Chem. Pharm. Bull.*, 20 (1972) 901.

Anderson, Wayne K. et al, *Synth. Commun.*, 19(13–14) (1989) 2237–2242.

Olomucki et al., *Biochim. Biophys. Acta*, 263 (1972) 213–216.

Otake, N. et al, *Tetrahedron Lett.*, 19 (1965) 1411–1419.

Patent: Kerin Seiyaku Kabushiki Kaisya, JP, A, 17189, 1968; *Referati vnyi Zhurnal. Khimiya.*, 1 (1970) N469P.

Umezawa et al, *J. Antibiot.*, 26 (1973) 625, 637.

Bycroft et al., *J. Antibiot.*, 22 (1969) 133–134.

Bycroft et al., *J. Chem. Soc.*(C), (1971) 3040–3046.

Marconi et al, *J. Antibiot.*, 23 (1970) 120–124.

Kretow et al, *J. Gen. Chem. USSR*, 32 (1962) 464.

Dorn et al, *Chem. Ber.*, 103 (1970) 2505–2511.

Andrewes et al, *Proc. R. Soc. London B*, 133 (1946) 20, 53 (Beilstein Registry ID Only).

Schubert, H. W. et al, *Arch. Pharm. Ber. Dtsch. Pharm. Ges.*, 301(10) (1968) 750–762.

Rodricks et al., *J. Org. Chem.*, 36 (1971) 46–48.

Stefanye et al, *J. Amer. Chem. Soc.*, 77 (1955) 761–762.

Goodman et al, *J. Org. Chem.*, 23 (1958) 1954–1956.

Goodman et al, *J. Org. Chem.*, 23 (1958) 1251–1255.

OXATHIADIAZOLE DERIVATIVES USFUL AS INOS INHIBITORS

This application is a divisional of U.S. patent application Ser. No. 08/898,110 filed Jul. 22, 1997, incorporated by reference now U.S. Pat. No. 5,981,556.

BACKGROUND OF THE INVENTION

1. Field of the Invention

The present invention relates to 1,3-diazolino and 1,3-diazolidino heterocycle derivatives and their use in therapy, in particular their use as nitric oxide synthase inhibitors.

2. Related Art

It has been known since the early 1980's that the vascular relaxation caused by acetylcholine is dependent on the presence of the vascular endothelium and this activity was ascribed to a labile humoral factor termed endothelium-derived relaxing factor (EDRF). The activity of nitric oxide (NO) as a vasodilator has been known for well over 100 years. In addition, NO is the active component of amylnitrite, glyceryltrinitrate and other nitrovasodilators. The recent identification of EDRF as NO has coincided with the discovery of a biochemical pathway by which NO is synthesized from the amino acid L-arginine by the enzyme NO synthase.

Nitric oxide is the endogenous stimulator of the soluble guanylate cyclase. In addition to endothelium-dependent relaxation, NO is involved in a number of biological actions including cytotoxicity of phagocytic cells and cell-to-cell communication in the central nervous system (see Moncada et al., Biochemical Pharmacology, 38, 1709–1715, 1989; Moncada et al., Pharmacological Reviews, 43, 109–142, 1991). Excess NO production appears to be involved in a number of pathological conditions, particularly conditions which involve systemic hypotension such as toxic shock, septic shock and therapy with certain cytokines (Kerwin et al., J. Medicinal Chemistry, 38, 4343–4362, 1995).

The synthesis of NO from L-arginine can be inhibited by the L-arginine analogue, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, Ca++/calmodulin dependent enzyme, located in the endothelium, that releases NO in response to receptor or physical stimulation.

(ii) a constitutive, Ca++/calmodulin dependent enzyme, located in the brain, that releases NO in response to receptor or physical stimulation.

(iii) a Ca++ independent enzyme which is induced after activation of vascular smooth muscle,macrophages, endothelial cells, and a number of other cells by endotoxin and cytokines. Once expressed this inducible NO synthase generates NO continuously for long periods.

The NO released by the two constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase (Knowles and Moncada, Biochem J., 298, 249–258, 1994 Billiar et al., Annals of Surgery, 221, 339–349, 1995; Davies et al., 1995)

There is also a growing body of evidence that NO may be involved in the degeneration of cartilage which takes place in cerain conditions such as arthritis and it is also known that NO synthesis is increased in rheumatoid arthritis and in osteoarthritis (McInnes et al., J. Exp. Med, 184, 1519–1524, 1996; Sakurai et al., J. Clin. Investig., 96, 2357–2363, 1995). Accordingly, conditions in which there is an advantage in inhibiting NO production from L-arginine include autoimmune and/or inflammatory conditions affecting the joints, for example arthritis, and also inflammatory bowel disease, cardivascular ischemia, diabetes, congestive heart failure, myocarditis, atherosclerosis, migraine, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (secondary to cardiac arrest), multiple sclerosis and other central nervous system disorders mediated by NO, for example Parkinson's disease and Alzheimer's disease, and other disorders mediated by NO including opiate tolerance in patients needing protracted opiate analgesics, and benzodiazepine tolerance in patients taking benzodiazepines, and other addictive behaviour, for example, nicotine and eating disorders (Kerwin et al., J. Medicinal Chemistry, 38, 4343–4362, 1995; Knowles and Moncada, Biochem J., 298, 249–258, 1994; Davies et al., 1995; Pfeilschifter et al., Cell Biology International, 20, 51–58, 1996).

Further conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy (E. Kelly et al., J. Partent. Ent. Nutri., 19, 234–238, 1995; S. Moncada and E. Higgs, FASEB J., 9, 1319–1330, 1995; R. G. Kilbourn et al, Crit. Care Med., 23, 1018–1024, 1995).

Some of the NO synthase inhibitors proposed for therapeutic use so far, and in particular L-NMMA, are non-selective; they inhibit both the constitutive and the inducible NO synthases. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

WO 96/35677, WO 96/33175, WO 96/15120, WO 95/11014, WO 95/11231, WO 95/25717, WO 95/24382, WO 94/12165, WO 94/14780, WO 93/13055, EP0446699A1 and U.S. Pat. No. 5,132,453 disclose compounds that inhibit nitric oxide synthesis and preferentially inhibit the inducible isoform of nitric oxide synthase. The disclosures of which are hereby incorporated by reference in their entirety as if written herein.

SUMMARY OF THE INVENTION

In a broad aspect, the present invention is directed to inhibiting or modulating nitric oxide synthesis in a subject in need of such inhibition or modulation by administering a compound which preferentially inhibits or modulates the inducible isoform of nitric oxide synthase over a constitutive isoform of nitric oxide synthase. It is also an object of the present invention to lower nitric oxide levels in a subject in need of such lowering.

Compounds of the present invention are represented by the following chemical formula:

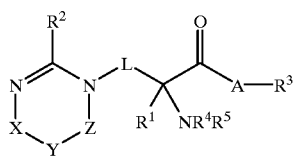

(I)

and pharmaceutically acceptable salts, wherein:
A is O, S or NR, wherein:
R is selected from the group consisting of hydrogen, lower alkyl, lower alkenyl, lower alkynyl, cycloalkyl, cycloalkenyl, heterocycle, aryl, alkylaryl, alkylheterocycle, all optionally substituted by one or more of alkyl, hydroxy, alkoxy, halogen, haloalkyl, cyano, amino, and nitro; or
NR together form a heterocycle;
$R^1$ is not present or is selected from the group consisting of hydrogen, lower alkyl, hydroxyalkyl, alkoxyalkyl, haloalkyl, cycloalkyl, heterocycle, aryl, alkylaryl, and alkylheterocycle, all optionally substituted by one or more of alkyl, hydroxy, alkoxy, halogen, haloalkyl, cyano, amino, and nitro;
$R^2$ is selected from the group consisting of amino, thioalkoxy, alkoxy, lower alkyl, lower alkenyl, lower alkynyl, cycloalkyl, cycloalkenyl, haloalkyl, aryl, heterocycle, alkylaryl, alkylheterocycle, alkoxyalkyl, and thioalkoxyalkyl all optionally substituted by one or more of alkyl, hydroxy, alkoxy, halogen, haloalkyl, cyano, amino, and nitro;
$R^3$ is not present or is selected from the group consisting of H, lower alkyl, lower alkenyl, lower alkynyl, cycloalkyl, cycloalkenyl, aryl, heterocycle, alkylaryl, and alkylheterocycle, all optionally substituted by one or more of halogen, haloalkyl, cyano, nitro, —$CO_2R$, and —COR; or
$R^3$ is selected from the group consisting of alkylhydroxy, alkylpolyhydroxy, alkyl(poly)oxyacyl, $CH_2C(=O)OR^6$, $CH_2C(=O)NHR^6$, $CH_2OC(=O)R^6$, and $CH_2OC(=O)JR^6$, the $CH_2$ is optionally substituted by one or more of lower alkyl, cycloalkyl, heterocycle, aryl, amidino, guanidino, $CO_2H$, amino, hydroxy, thiol, halogen, haloalkyl, cyano, and nitro;
J is selected from the group consisting of O, S, $CH_2$, $CHR^6$, $C(R^6)_2$, NH, and $NR^6$;
$R^4$ is selected from the group consisting of H, $S(O)R^7$, $SO_2R^7$, $CH_2OC(O)$—$R^7$, and $C(O)$—$R^7$ where $C(O)$—$R^7$ represents natural or synthetic amino acids or $R^7$ is defined as below, or $R^4$ and $R^3$ taken together comprise a 5- or 6-membered heterocyclic ring containing two or more heteroatoms, optionally substituted with alkyl or oxygen functions or both, including carbonyl, or taken together comprise a metal complex containing a divalent cation, or a boron complex;
$R^5$ is $R^6$ or $C(O)$—$R^6$;
$R^6$ is selected from the group consisting of hydrogen, alkyl, alkenyl, alkynyl, cycloalkyl, heterocycle, and aryl, all optionally substituted by one or more alkyl, hydroxy, alkoxy, halogen, trifluoromethyl, nitro, cyano, or amino groups;
$R^7$ is selected from the group consisting of substituted dihydropyridyl, alkyl, thioalkoxy, alkoxy, amino, and cycloalkoxy, all optionally substituted with one or more of amino, alkyl, alkylaryl, heterocycle, alkylheterocycle, alkylmercaptoalkyl, which may optionally be substituted with one or more of hydroxy, amino, guanidino, iminoalkyl;
L is selected from the group consisting of lower alkylenes, lower alkenylenes and lower alkynylenes, which may optionally be substituted by one or more alkyl, alkoxy, hydroxy, halogen, trifluoromethyl, nitro, cyano, or amino groups; or
L is selected from the group consisting of the formula —$(CH_2)_kQ(CH_2)_t$— where k is 1, 2 or 3, t is 1, 2 or 3 and Q is O, Se, $Se(O)_g$, $SiE_2$ where E is lower alkyl, aryl, $S(O)_g$ where g is 0, 1 or 2, or NR; or
L is selected from the group consisting of the formula —$(CH_2)_mT(CH_2)_n$— where m is 0, 1 or 2, n is 0, 1 or 2, T is a 3 to 6 membered carbocyclic or heterocyclic ring or aromatic ring which may optionally be substituted by one or more substituents selected from the group consisting of lower alkyl, lower alkoxy, hydroxy, halogen, nitro, cyano, trifluoroalkyl and amino;
X is selected from the group consisting of O, S, $C(=O)$, $C(=S)$, $C=C(R^6)_2$, $S(=O)$, $SO_2$, and $C(R^6)_2$;
Y is a bond or is selected from the group consisting of O, S, $C(=O)$, $C(=S)$, $C=C(R^6)_2$, $S(=O)$, $SO_2$, and $C(R^6)_2$;
Z is selected from the group consisting of O, S, $C(=O)$, $C(=S)$, $C=C(R^6)_2$, $S(=O)$, $SO_2$, and $C(R^6)_2$.

It is an object of the present invention to provide compounds that have usefulness as inhibitors of nitric oxide synthase. These compounds also preferentially inhibit the inducible form over a constitutive form.

DETAILED DESCRIPTION OF THE INVENTION

Compounds of the present invention are represented by the following chemical formula:

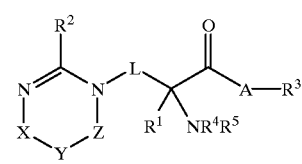

(I)

and pharmaceutically acceptable salts, wherein:
A is O, S, or NR, wherein:
R is selected from the group consisting of hydrogen, lower alkyl, lower alkenyl, lower alkynyl, cycloalkyl, cycloalkenyl, heterocycle, aryl, alkylaryl, alkylheterocycle, all optionally substituted by one or more of alkyl, hydroxy, alkoxy, halogen, haloalkyl, cyano, amino, nitro; or
NR together form a heterocycle;
$R^1$ is not present or is selected from the group consisting of hydrogen, lower alkyl, hydroxyalkyl, alkoxyalkyl, haloalkyl, cycloalkyl, heterocycle, aryl, alkylaryl, and alkylheterocycle, all optionally substituted by one or more of alkyl, hydroxy, alkoxy, halogen, haloalkyl, cyano, amino, and nitro;

$R^2$ is selected from the group consisting of amino, thioalkoxy, alkoxy, lower alkyl, lower alkenyl, lower alkynyl, cycloalkyl, cycloalkenyl, haloalkyl, aryl, heterocycle, alkylaryl, alkylheterocycle, alkoxyalkyl, and thioalkoxyalkyl all optionally substituted by one or more of alkyl, hydroxy, alkoxy, halogen, haloalkyl, cyano, amino, and nitro;

$R^3$ is not present or is selected from the group consisting of H, lower alkyl, lower alkenyl, lower alkynyl, cycloalkyl, cycloalkenyl, aryl, heterocycle, alkylaryl, and alkylheterocycle, all optionally substituted by one or more of halogen, haloalkyl, cyano, nitro, —$CO_2R$, and —COR; or $R^3$ is selected from the group consisting of alkylhydroxy, alkylpolyhydroxy, alkyl(poly)oxyacyl, $CH_2C(=O)OR^6$, $CH_2C(=O)NHR^6$, $CH_2OC(=O)R^6$, and $CH_2OC(=O)JR^6$, the $CH_2$ is optionally substituted by one or more of lower alkyl, cycloalkyl, heterocycle, aryl, amidino, guanidino, $CO_2H$, amino, hydroxy, thiol, halogen, haloalkyl, cyano, and nitro;

J is selected from the group consisting of O, S, $CH_2$, $CHR^6$, $C(R^6)_2$, NH, and $NR^6$;

$R^4$ is selected from the group consisting of H, $S(O)R^7$, $SO_2R^7$, $CH_2OC(O)$—$R^7$, and $C(O)$—$R^7$ where $C(O)$—$R^7$ represents natural or synthetic amino acids or $R^7$ is defined as below, or $R^4$ and $R^3$ taken together comprise a 5- or 6-membered heterocyclic ring containing two or more heteroatoms, optionally substituted with alkyl or oxygen functions or both, including carbonyl, or taken together comprise a metal complex containing a divalent cation, or a boron complex;

$R^5$ is $R^6$ or $C(O)$—$R^6$;

$R^6$ is selected from the group consisting of hydrogen, alkyl, alkenyl, alkynyl, cycloalkyl, heterocycle, and aryl, all optionally substituted by one or more alkyl, hydroxy, alkoxy, halogen, trifluoromethyl, nitro, cyano, or amino groups;

$R^7$ is selected from the group consisting of substituted dihydropyridyl, alkyl, thioalkoxy, alkoxy, amino, and cycloalkoxy, all optionally substituted with one or more of amino, alkyl, alkylaryl, heterocycle, alkylheterocycle, and alkylmercaptoalkyl, which may optionally be substituted with one or more of hydroxy, amino, guanidino, and iminoalkyl;

L is selected from the group consisting of lower alkylenes, lower alkenylenes and lower alkynylenes which may optionally be substituted by one or more and alkyl, alkoxy, hydroxy, halogen, trifluoromethyl, nitro, cyano, or amino groups; or L is selected from the group consisting of the formula —$(CH_2)_kQ(CH_2)_t$— where k is 1, 2 or 3, t is 1, 2 or 3 and Q is O, Se, $Se(O)_g$, $SiE_2$ where E is lower alkyl, aryl, $S(O)_g$ where g is 0, 1 or 2, or NR; or L is selected from the group consisting of the formula —$(CH_2)_mT(CH_2)_n$— where m is 0, 1 or 2, n is 0, 1 or 2, T is a 3 to 6 membered carbocyclic or heterocyclic ring, or aromatic ring which may optionally be substituted by one or more substituents selected from the group consisting of lower alkyl, lower alkoxy, hydroxy, halogen, nitro, cyano, trifluoroalkyl and amino;

X is selected from the group consisting of O, S, C(=O), C(=S), C=$C(R^6)_2$, S(=O), $SO_2$, and $C(R^6)_2$;

Y is a bond or is selected from the group consisting of O, S, C(=O), C(=S), C=$C(R^6)_2$, S(=O), $SO_2$, and $C(R^6)_2$;

Z is selected from the group consisting of O, S, C(=O), C(=S), C=$C(R^6)_2$, S(=O), $SO_2$, and $C(R^6)_2$.

A preferred embodiment of the present invention is a compound of the formula (I) and pharmaceutically acceptable salts, wherein:

A is O, S, or NR, wherein:
R is selected from the group consisting of hydrogen, lower alkyl, lower alkenyl, lower alkynyl, cycloalkyl, cycloalkenyl, heterocycle, aryl, alkylaryl, and alkylheterocycle, all optionally substituted by one or more of alkyl, hydroxy, alkoxy, halogen, haloalkyl, cyano, amino, and nitro; or NR together form a heterocycle;

$R^1$ is not present or is selected from the group consisting of hydrogen, lower alkyl, hydroxyalkyl, alkoxyalkyl, haloalkyl, cycloalkyl, heterocycle, aryl, alkylaryl, and alkylheterocycle, all optionally substituted by one or more of alkyl, hydroxy, alkoxy, halogen, haloalkyl, cyano, amino, and nitro;

$R^2$ is selected from the group consisting of amino, thioalkoxy, alkoxy, lower alkyl, lower alkenyl, lower alkynyl, cycloalkyl, cycloalkenyl, haloalkyl, aryl, heterocycle, alkylaryl, alkylheterocycle, alkoxyalkyl, and thioalkoxyalkyl all optionally substituted by one or more of alkyl, hydroxy, alkoxy, halogen, haloalkyl, cyano, amino, and nitro;

$R^3$ is not present or is selected from the group consisting of H, lower alkyl, lower alkenyl, lower alkynyl, cycloalkyl, cycloalkenyl, aryl, heterocycle, alkylaryl, and alkylheterocycle, all optionally substituted by one or more of halogen, haloalkyl, cyano, nitro, —$CO_2R$, and —COR; or $R^3$ is selected from the group consisting of alkylhydroxy, alkylpolyhydroxy, alkyl(poly)oxyacyl, $CH_2C(=O)OR^6$, $CH_2C(=O)NHR^6$, $CH_2OC(=O)R^6$, and $CH_2OC(=O)JR^6$, the $CH_2$ is optionally substituted by one or more of lower alkyl, cycloalkyl, heterocycle, aryl, amidino, guanidino, $CO_2H$, amino, hydroxy, thiol, halogen, haloalkyl, cyano, and nitro;

J is selected from the group consisting of O, S, $CH_2$, $CHR^6$, $C(R^6)_2$, NH, and $NR^6$;

$R^4$ is selected from the group consisting of H, $S(O)R^7$, $SO_2R^7$, $CH_2OC(O)$—$R^7$, and $C(O)$—$R^7$ where $C(O)$—$R^7$ represents natural or synthetic amino acids or $R^7$ is defined as below, or $R^4$ and $R^3$ taken together comprise a 5- or 6-membered heterocyclic ring containing two or more heteroatoms, optionally substituted with alkyl or oxygen functions or both, including carbonyl, or taken together comprise a metal complex containing a divalent cation, or a boron complex;

$R^5$ is $R^6$ or $C(O)$—$R^6$;

$R^6$ is selected from the group consisting of hydrogen, alkyl, alkenyl, alkynyl, cycloalkyl, and heterocycle, and aryl, all optionally substituted by one or more alkyl, hydroxy, alkoxy, halogen, trifluoromethyl, nitro, cyano, or amino groups;

$R^7$ is selected from the group consisting of substituted dihydropyridyl, alkyl, thioalkoxy, alkoxy, amino, and cycloalkoxy, all optionally substituted with one or more of amino, alkyl, alkylaryl, heterocycle, alkylheterocycle, and alkylmercaptoalkyl, which may optionally be substituted with one or more of hydroxy, amino, guanidino, and iminoalkyl;

L is selected from the group consisting of lower alkylenes, lower alkenylenes and lower alkynylenes which may optionally be substituted by one or more alkyl, alkoxy, hydroxy, halogen, trifluoromethyl, nitro, cyano, or amino groups; or L is selected from the group consisting of the formula —$(CH_2)_k Q(CH_2)_t$— where k is 1, 2 or 3, t is 1, 2 or 3 and Q is O, Se, $Se(O)_g$, $SiE_2$ where E is lower alkyl, aryl, $S(O)_g$ where g is 0, 1 or 2, or NR; or L is selected from the group consisting of the formula —$(CH_2)_m T(CH_2)_n$— where m is 0, 1 or 2, n is 0, 1 or 2, T is a 3 to 6 membered carbocyclic or heterocyclic ring, or aromatic ring which may optionally be substituted by one or more substituents selected from the group consisting of lower alkyl, lower alkoxy, hydroxy, halogen, nitro, cyano, trifluoroalkyl and amino;

X is selected from the group consisting of O, S, C(=O), C(=S), C=C($R^6$)$_2$, S(=O), SO$_2$, and C($R^6$)$_2$;

Y is a bond or is selected from the group consisting of O, S, C(=O), C(=S), C=C($R^6$)$_2$, S(=O), SO$_2$, and C($R^6$)$_2$;

Z is selected from the group consisting of O, S, C(=O), C(=S), C=C($R^6$)$_2$, S(=O), SO$_2$, and C($R^6$)$_2$.

A further preferred embodiment of the present invention is a compound of the formula (I) and pharmaceutically acceptable salts, wherein:

A is O, S, or NR, wherein:
  R is selected from the group consisting of hydrogen, lower alkyl, lower alkenyl, lower alkynyl, cycloalkyl, cycloalkenyl, heterocycle, aryl, alkylaryl, and alkylheterocycle, all optionally substituted by one or more of alkyl, hydroxy, cyano, amino, nitro; or
  NR together form a heterocycle;
  $R^1$ is not present or is selected from the group consisting of hydrogen, lower alkyl, hydroxyalkyl, alkoxyalkyl, haloalkyl, cycloalkyl, heterocycle, aryl, alkylaryl, and alkylheterocycle;
  $R^2$ is selected from the group consisting of amino, thioalkoxy, alkoxy, lower alkyl, lower alkenyl, lower alkynyl, cycloalkyl, cycloalkenyl, haloalkyl, aryl, heterocycle, alkylaryl, alkylheterocycle, alkoxyalkyl, and thioalkoxyalkyl all optionally substituted by one or more of alkyl, hydroxy, cyano, amino, and nitro;
  $R^3$ is not present or is selected from the group consisting of H, lower alkyl, lower alkenyl, lower alkynyl, cycloalkyl, cycloalkenyl, aryl, heterocycle, alkylaryl, and alkylheterocycle, all optionally substituted by one or more of cyano, nitro, —CO$_2$R, and —COR; or
  $R^3$ is selected from the group consisting of CH$_2$C(=O)OR$^6$, CH$_2$C(=O)NHR$^6$, CH$_2$OC(=O)R$^6$, and CH$_2$OC(=O)JR$^6$, the CH$_2$ is optionally substituted by one or more of lower alkyl, cycloalkyl, heterocycle, aryl, amidino, guanidino, CO$_2$H, amino, hydroxy, thiol, halogen, haloalkyl, cyano, and nitro;
  J is selected from the group consisting of O, S, CH$_2$, CHR$^6$, C(R$^6$)$_2$, NH, and NR$^6$;
  $R^4$ is selected from the group consisting of H, S(O)R$^7$, SO$_2$R$^7$, CH$_2$OC(O)—R$^7$, and C(O)—R$^7$ where C(O)—R$^7$ represents natural or synthetic amino acids or $R^7$ is defined as below, or $R^4$ and $R^3$ taken together comprise a 5- or 6-membered heterocyclic ring containing two or more heteroatoms;

$R^5$ is $R^6$ or C(O)—$R^6$;
$R^6$ is selected from the group consisting of hydrogen, alkyl, alkenyl, alkynyl, cycloalkyl, heterocycle, and aryl, all optionally substituted by one or more alkyl, hydroxy, nitro, cyano, and amino groups;
$R^7$ is selected from the group consisting of substituted dihydropyridyl, alkyl, thioalkoxy, alkoxy, amino, and cycloalkoxy, all optionally substituted with one or more of amino, alkyl, alkylaryl, heterocycle, alkylheterocycle, and alkylmercaptoalkyl, which may optionally be substituted with one or more of hydroxy, amino, guanidino, and iminoalkyl;

L is selected from the group consisting of lower alkylenes, lower alkenylenes and lower alkynylenes which may optionally be substituted by one or more alkyl, hydroxy, nitro, cyano, and amino groups; or L is selected from the group consisting of the formula —$(CH_2)_k Q(CH_2)_t$— where k is 1, 2 or 3, t is 1, 2 or 3 and Q is O, Se, $Se(O)_g$, $SiE_2$ where E is lower alkyl, aryl, $S(O)_g$ where g is 0, 1 or 2, or NR; or L is selected from the group consisting of the formula —$(CH_2)_m T(CH_2)_n$— where m is 0, 1 or 2, n is 0, 1 or 2, T is a 3 to 6 membered carbocyclic or heterocyclic ring, or aromatic ring which may optionally be substituted by one or more substituents selected from the group consisting of lower alkyl, lower alkoxy, hydroxy, halogen, nitro, cyano, trifluoroalkyl and amino;

X is selected from the group consisting of O, S, C(=O), C(=S), C=C($R^6$)$_2$, S(=O), SO$_2$, and C($R^6$)$_2$;

Y is a bond or is selected from the group consisting of O, S, C(=O), C(=S), C=C($R^6$)$_2$, S(=O), SO$_2$, and C($R^6$)$_2$;

Z is selected from the group consisting of O, S, C(=O), C(=S), C=C($R^6$)$_2$, S(=O), SO$_2$, and C($R^6$)$_2$.

Another preferred embodiment of the present invention is a compound of the formula (I) and pharmaceutically acceptable salts; wherein:

A is O, S, or NR, wherein:
  R is selected from the group consisting of hydrogen, lower alkyl, lower alkenyl, lower alkynyl, cycloalkyl, cycloalkenyl, heterocycle, aryl, alkylaryl, alkylheterocycle; or
  NR together form a heterocycle;
  $R^1$ is not present or is hydrogen or lower alkyl;
  $R^2$ is selected from the group consisting of amino, thioalkoxy, alkoxy, lower alkyl, lower alkenyl, lower alkynyl, cycloalkyl, cycloalkenyl, haloalkyl, aryl, heterocycle, alkylaryl, alkylheterocycle, alkoxyalkyl, and thioalkoxyalkyl all optionally substituted by one or more of alkyl, hydroxy, cyano, amino, and nitro;
  $R^3$ is not present or is selected from the group consisting of H. lower alkyl, lower alkenyl, lower alkynyl, cycloalkyl, cycloalkenyl, aryl, heterocycle, alkylaryl, and alkylheterocycle, all optionally substituted by one or more of —CO$_2$R, and —COR; or
  $R^3$ is selected from the group consisting of CH$_2$C(=O)OR$^6$, CH$_2$C(=O)NHR$^6$, CH$_2$OC(=O)R$^6$, and CH$_2$OC(=O)JR$^6$, the CH$_2$ is optionally substituted by one or more of lower alkyl, cycloalkyl, heterocycle, aryl, amidino, guanidino, CO$_2$H, amino, hydroxy, thiol, halogen, haloalkyl, cyano, and nitro;
  J is O, S, or NH;
  $R^4$ is H, CH$_2$OC(O)—$R^7$, or C(O)—$R^7$;
  $R^5$ is $R^6$ or C(O)—$R^6$;

$R^6$ is selected from the group consisting of hydrogen, alkyl, alkenyl, alkynyl, cycloalkyl, heterocycle, and aryl;

$R^7$ is selected from the group consisting of substituted dihydropyridyl, alkyl, thioalkoxy, alkoxy, amino, and cycloalkoxy, all optionally substituted with one or more of amino, alkyl, alkylaryl, heterocycle, alkylheterocycle, alkylmercaptoalkyl, which may optionally be substituted with one or more of hydroxy, amino, guanidino, and iminoalkyl;

L is selected from the group consisting of lower alkylenes and lower alkenylenes which may optionally be substituted by one or more alkyl, hydroxy, nitro, cyano, or amino groups; or L is selected from the group consisting of the formula —$(CH_2)_kQ(CH_2)_t$— where k is 1, 2 or 3, t is 1, 2 or 3 and Q is O, Se, $Se(O)_g$, $SiE_2$ where E is lower alkyl, aryl, $S(O)_g$ where g is 0, 1 or 2, or NR; or L is selected from the group consisting of the formula —$(CH_2)_mT(CH_2)_n$— where m is 0, 1 or 2, n is 0, 1 or 2, T is a 3 to 6 membered carbocyclic or heterocyclic ring, or aromatic ring which may optionally be substituted by one or more substituents selected from the group consisting of lower alkyl, lower alkoxy, hydroxy, halogen, nitro, cyano, trifluoroalkyl and amino;

X is selected from the group consisting of O, S, C(=O), C(=S), C=C($R^6$)$_2$, S(=O), SO$_2$, and C($R^6$)$_2$;

Y is a bond or is selected from the group consisting of O, S, C(=O), C(=S), C=C($R^6$)$_2$, S(=O), SO$_2$, and C($R^6$)$_2$;

Z is selected from the group consisting of O, S, C(=O), C(=S), C=C($R^6$)$_2$, S(=O), SO$_2$, and C($R^6$)$_2$.

Another preferred embodiment of the present invention is a compound of the formula (I) and pharmaceutically acceptable salts; wherein:

A is O or NR;

R is selected from the group consisting of heterocycle, aryl, alkylaryl, and alkylheterocycle;

$R^1$ is hydrogen;

$R^2$ is selected from the group consisting of amino, lower alkyl, lower alkenyl, lower alkynyl, cycloalkyl, cycloalkenyl, haloalkyl, aryl, heterocycle, alkylaryl, alkylheterocycle, alkoxyalkyl, and thioalkoxyalkyl;

$R^3$ is not present or is selected from the group consisting of H. lower alkyl, aryl, heterocycle, alkylaryl, and alkylheterocycle; or $R^3$ is CH$_2$C(=O)OR$^6$ or CH$_2$C(=O)NHR$^6$, the CH$_2$ is optionally substituted by one or more of lower alkyl, cycloalkyl, heterocycle, aryl, amidino, guanidino, CO$_2$H, amino, hydroxy, thiol, halogen, haloalkyl, cyano, and nitro;

$R^4$ is H, CH$_2$OC(O)—$R^7$ or C(O)—$R^7$;

$R^5$ is $R^6$ or C(O)—$R^6$;

$R^6$ is hydrogen, alkyl, heterocyclic, or aryl, or;

$R^7$ is alkyl, optionally substituted with one or more of amino, alkyl, alkylaryl, heterocycle, alkylheterocycle, alkylmercaptoalkyl, hydroxy, guanidino, and iminoalkyl;

L is selected from the group consisting of lower alkylenes and lower alkenylenes; or L is selected from the group consisting of the formula —$(CH_2)_kQ(CH_2)_t$— where k is 1, 2 or 3, t is 1, 2 or 3 and Q is O, Se, $Se(O)_g$, $SiE_2$ where E is lower alkyl, aryl, $S(O)_g$ where g is 0, 1 or 2, or NR where R is H or lower alkyl; or L is selected from the group consisting of the formula —$(CH_2)_mT(CH_2)_n$— where m is 0, 1 or 2, n is 0, 1 or 2, T is a 3 to 6 membered carbocyclic ring, heterocyclic ring, or aromatic ring;

X is O, S, or C(=O);

Y is a bond or is O, S, or C(=O);

Z is O, S, or C(=O).

Another preferred embodiment of the present invention is a compound of the formula (I) and pharmaceutically acceptable salts; wherein:

A is O;

$R^1$ is hydrogen;

$R^2$ is lower alkyl;

$R^3$ is hydrogen or a lower alkyl having 1 to 4 carbon atoms;

$R^4$ is hydrogen;

$R^5$ is hydrogen;

L is an alkylene having 3 to 5 carbon atoms;

X is O;

Y is a bond;

Z is C(=O).

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, ρ-toluenesulphonic, benzenesulphonic and isethionic acids. Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical composition. According to a further aspect, the present invention provides a pharmaceutical composition comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tertbutyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "heterocyclic or heterocycle" means a saturated or unsaturated cyclic hydrocarbon radical with 4 to about 10 carbon atoms, preferably about 5 to about 6; wherein 1 to about 3 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, thiazolyl, imidazolyl, indolyl, thiophenyl, furanyl, tetrazolyl, 2-pyrrolinyl, 3-pyrrolinyl, pyrrolindinyl, 1,3-dioxolanyl, 2-imidazonlinyl, imidazolidinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

The term "aryl" means an aromatic hydrocarbon radical of 6 to about 14 carbon atoms, preferably 6 to about 10 carbon atoms. Examples of suitable aromatic hydrocarbon radicals include phenyl, naphthyl, and the like.

The terms "cycloalkyl" or "cycloalkenyl" means an alicyclic radical in a ring with 3 to about 10 carbon atoms, and preferably from 3 to about 6 carbon atoms. Examples of suitable alicyclic radicals include cyclopropyl, cyclopropenyl, cyclobutyl, cyclopentyl, cyclohexyl, 2-cyclohexen-1-ylenyl, cyclohexenyl and the like.

The term "alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, isobutoxy, sec-butoxy, tert-butoxy and the like.

The terms "lower alkylene", "lower alkenylene" and "lower alkynylene" refers to hydrocarbons containing 2 to 10 carbon atoms, preferably 2 to 8 carbon atoms, and more preferably 2 to 6 carbon atoms.

The term "halogen" means fluorine, chlorine, bromine or iodine.

The term "haloalkyl", means an alkyl radical as defined above, with halogen radicals replacing one or more of the hydrogens.

The term "prodrug" refers to a compound that is made more active in vivo.

As used herein, reference to "treatment" of a patient is intended to include prophylaxis.

All references, patents or applications, U.S. or foreign, cited in the application are hereby incorporated by reference as if written herein.

The following general synthetic sequences are useful in making the present invention.

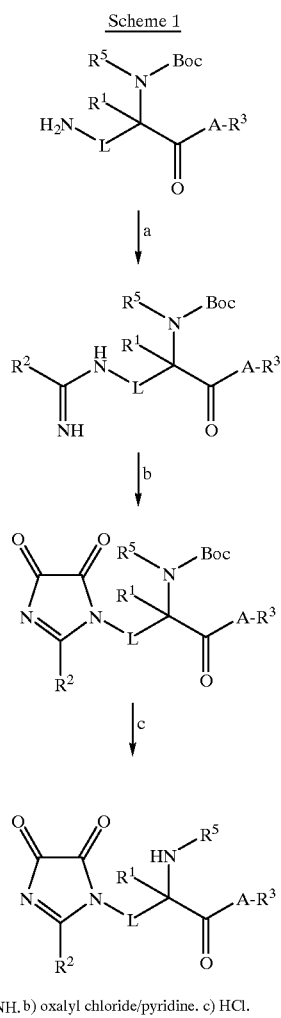

a) R²C(OEt)═NH. b) oxalyl chloride/pyridine. c) HCl.

Scheme 2

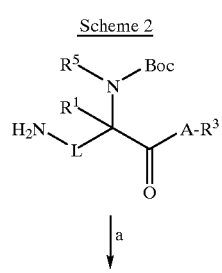

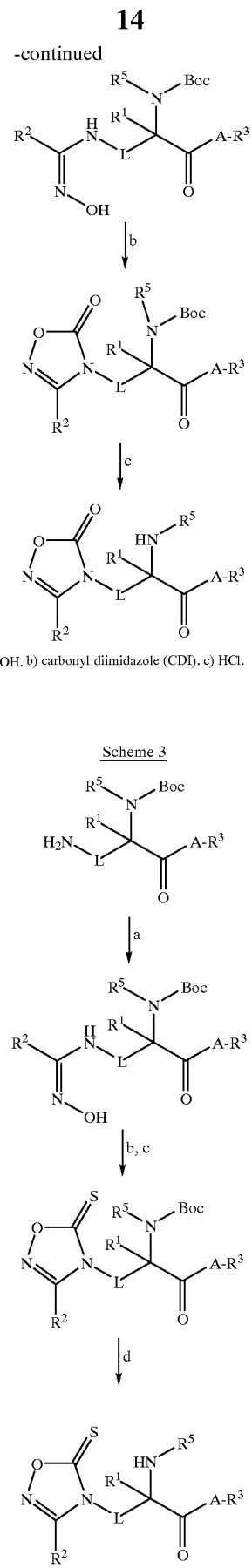

a) R²C(Cl)═NOH. b) carbonyl diimidazole (CDI). c) HCl.

a) $R^2C(Cl)=NOH$. b) thiocarbonyl diimidazole (CDI). c) DBU. d) HCl.
Scheme 4
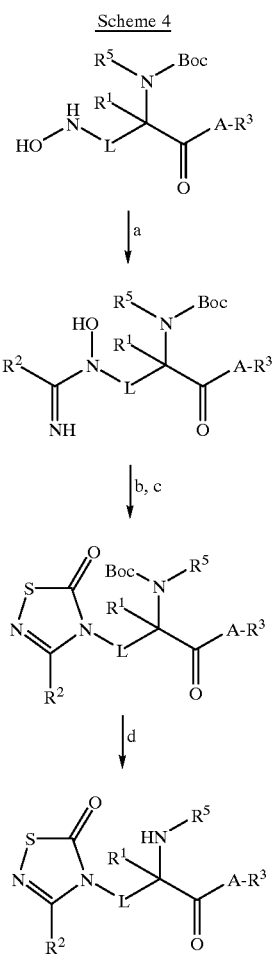
a) $R^2C(OEt)=NH$. b) thiocarbonyldiimidazole. c) silica gel or $BF_3 \cdot OEt_2$. d) HCl.
Scheme 5
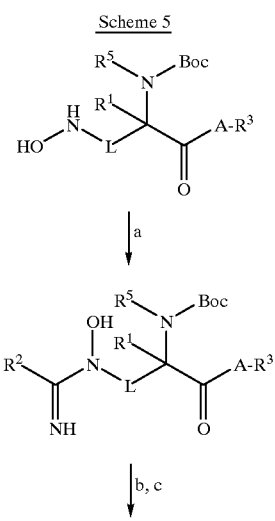
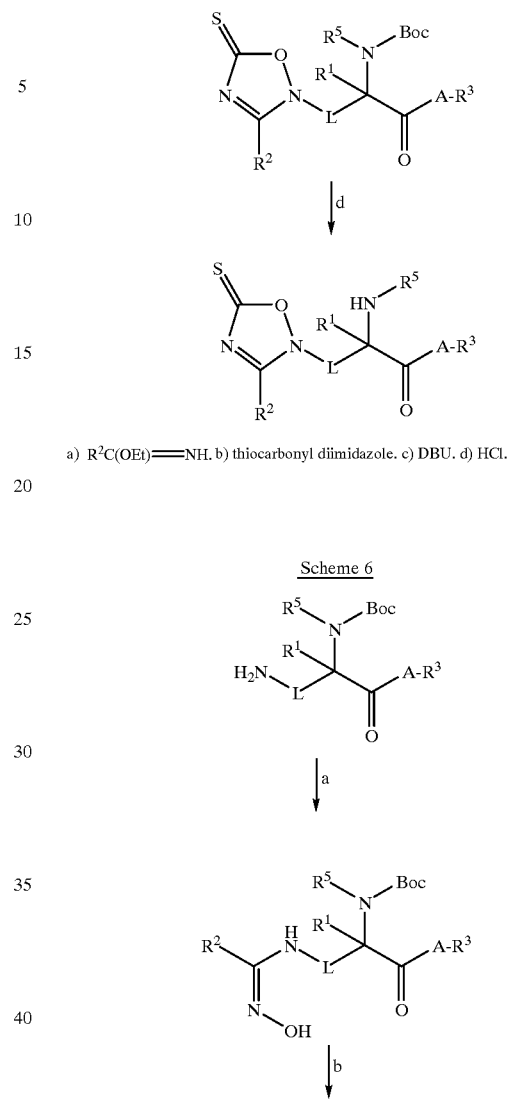
a) $R^2C(OEt)=NH$. b) thiocarbonyl diimidazole. c) DBU. d) HCl.
Scheme 6
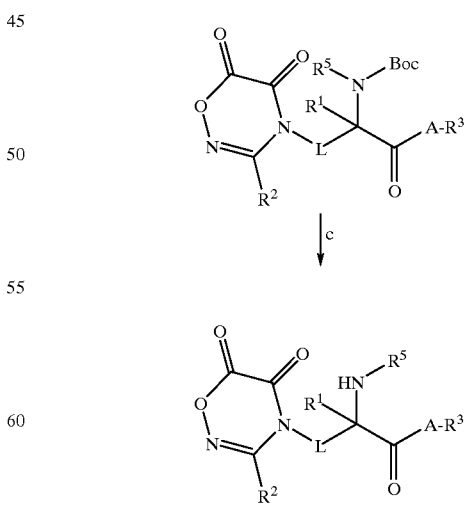
a) $R^2C(Cl)=NOH$. b) oxalyl chloride/pyridine. c) HCl.

Scheme 7
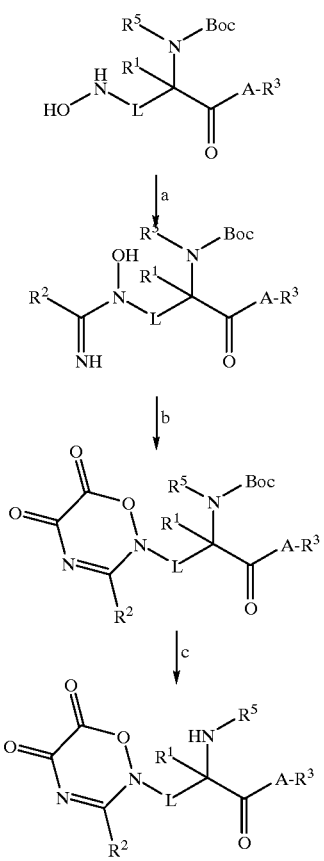
a) $R^2C(OEt)=NH$. b) oxalyl chloride/pyridine. c) HCl.
Scheme 8
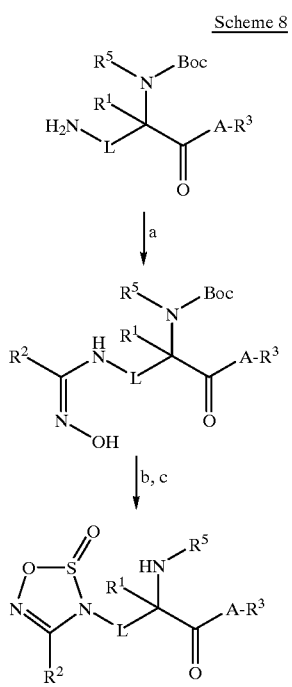
a) $R^2C(Cl)=NOH$. b) thionyl chloride/pyridine. c) HCl
Scheme 9
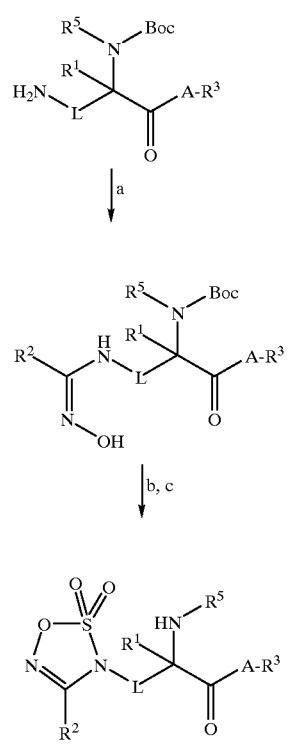
a) $R^2C(Cl)=NOH$. b) sulfuryl chloride/pyridine. c) HCl.
Scheme 10
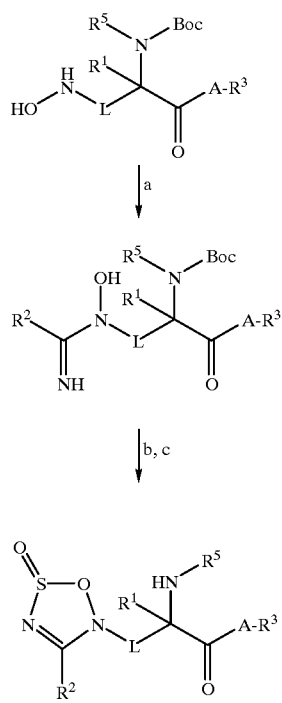
a) $R^2C(OEt)=NH$. b) thionyl chloride/pyridine. c) HCl.

Scheme 11

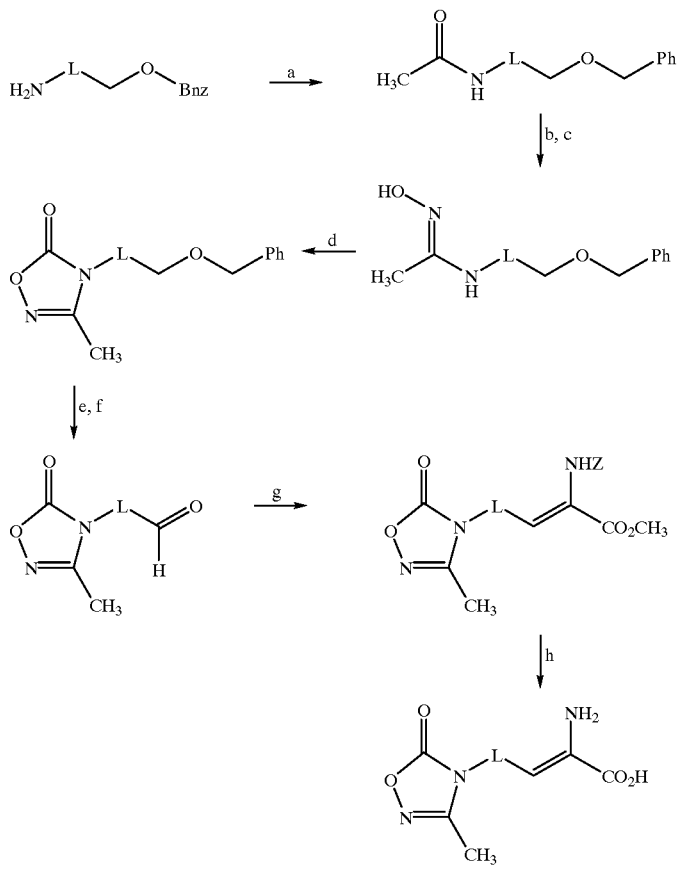

a) acetic anhydride. b) (CH$_3$)$_3$O$^+$BF$_4^-$. c) NH$_2$OH• HCl.
d) CDI. e) HBr/AcOH. f) pyridinium chlorochromate.
g) (CH$_3$)$_2$P(O)CH(NHZ)CO$_2$CH$_3$. h) HBr/AcOH.

Without further elaboration, it is believed that one skilled in the art can, using the preceeding description, utilize the present invention to its fullest extent. Therefore the following preferred specific embodiments are to be construed as merely illustrative and not limitative of the remainder of the disclosure in any way whatsoever.

All experiments were performed under either dry nitrogen or argon. All solvents and reagents were used without further purification unless otherwise noted. The routine work-up of the reactions involved the addition of the reaction mixture to a mixture of either neutral, or acidic, or basic aqueous solutions and organic solvent. The aqueous layer was extracted n times (x) with the indicated organic solvent. The combined organic extracts were washed n times (x) with the indicated aqueous solutions, dried over anhydrous Na$_2$SO$_4$, filtered, concentrated in vacuo, and purified as indicated. Separations by column chromatography were achieved with conditions described by Still. (Still, W. C.; Kahn, M.; Mitra, A. Rapid Chromatograhic Technique for Preparative Separation with Moderate Resolution. *J. Org. Chem.*, 1978, 43, 2923–2925.) The hydrochloride salts were made from 1N HCl, HCl in ethanol (EtOH), 2 N in MeOH, or 6 N HCl in dioxane. Thin layer chromatograms were run on 0.25 mm EM precoated plates of silica gel 60 F254. High performance liquid chromatograms (HPLC) were obtained from C-8 or C-18 reverse phase columns which were obtained from several vendors. Analytical samples were dried in an Abderhalden apparatus at either 56° C. or 78° C. $^1$H NMR spectra were obtained from either General Electric QE-300 or Varian VXR 400 MHz spectrometers with tetramethylsilane as an internal standard. $^{13}$C NMR spectra were obtained from a Varian spectrometer at 125.8 MHz with tetramethylsilane as an internal standard.

EXAMPLE 1

αS-[[(1,1-dimethylethoxy)carbonyl]amino]-4,5-dihydro-3-methyl-5-oxo-1,2,4-oxadiazole-4-hexanoic acid

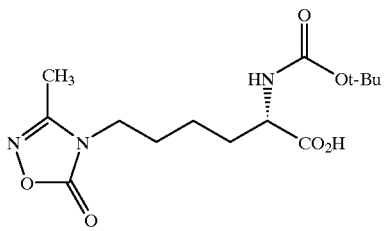

EXAMPLE 1A

To a 125 mL flask was added 3 g (0.012 mol) of α-Boc-L-lysine and 70 mL of water. This solution was adjusted to pH=9.5 by addition of 2.5 N NaOH. To this solution was added portion wise, 2.3 g of chloroacetaldoxime which was prepared immediately prior to use by the reaction of 3.55 g (0.06 mol) of acetaldoxime with 10.4 g (0.78 mol) of N-chlorosuccinimide in 65 mL of N,N-dimethylformamide at 0° C. The chloroacetaldoxime was isolated after three hours by extracting into diethyl ether and washing with aqueous NaCl. Drying with $MgSO_4$, filtration and concentration under 30° C. afforded the chloroacetaldoxime as a pale yellow oil. During the chloroacetaldoxime addition, the pH was kept at 9.5 via concomitant addition of 2.5 N NaOH. After the addition was complete, the solution was allowed to stand at 25° C. for 25 minutes. The solution was then adjusted to pH=7.5 with 1N HCl and poured onto a Dowex 50 Cation exchange column. The column was washed with water. The Boc-protected product was then eluted with 10% aqueous pyridine. $^1$H-NMR($D_2O$) 1.25 (s, 9H); 1.4–1.65 (m, 6H), 2.05 (s, 3H), 3.22 (t, 2H), 3.75 (m, 1H); Mass Spectrum, M+H=304.

EXAMPLE 1B

The hydroxamidine was allowed to react with carbonyl diimidazole in methylene chloride in the presence of diisopropylethylamine (DIEA). The reaction mixture was diluted with dilute aqueous HCl and extracted with ethyl acetate. The organic layer was washed with dilute HCl, dried ($MgSO_4$), filtered and concentrated to afford the title product as a white foam. $^1$H-NMR($D_2O$) 1.4 (s, 9H); 1.6–2.0 (m, 6H), 2.12 (s, 3H), 3.55 (t, 2H), 4.3 (m, 1H), 5.2 (bd, 1H).

Elemental Analysis Calcd. for $C_{14}H_{23}N_3O_6$+0.25 $H_2O$: C, 50.37; H, 7.10; N, 12.59. Found: C, 50.69; H, 7.21; N, 11.65.

EXAMPLE 2

αS-amino-4,5-dihydro-3-methyl-5-oxo-1,2,4-oxadiazole-4-hexanoic acid, monohydrochloride

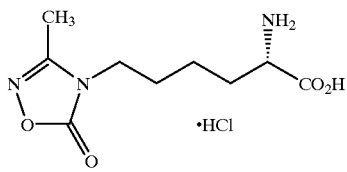

The title product of EXAMPLE 1 was allowed to stand for 18 hours at 25° C. in 3N HCl. Removal of the solvent in vacuo afford the title product as an off-white foam. $^1$H-NMR ($D_2O$) 1.35–1.5 (m, 2H), 1.62 (p, 2H), 1.8–2.0 (m, 2H), 2.2 (s, 3H), 3.55 (t, 2H), 3.95 (t, 1H). $^{13}$C-NMR($D_2O$) 9.53, 21.39, 27.05, 29.25, 41.90, 52.68, 158.83, 161.09, 171.93. Mass Specrtal analysis for $C_9H_{15}N_3O_4$: M+H=230.

Elemental Analysis Calcd. for $C_9H_{16}N_3O_6Cl_1$+2.25 $H_2O$: C, 35.30; H, 6.75; N, 13.72. Found: C, 35.26; H, 6.24; N, 13.77.

EXAMPLE 3 ethyl αS-amino-4,5-dihydro-3-methyl-5-oxo-1,2,4-oxadiazole-4-hexanoate, monohydrochloride

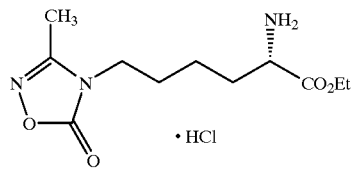

To a solution of 1 g (0.004 mol) of EXAMPLE 2 in 100 mL of ethanol is added a small amount of anhydrous HCl. This solution is allowed to stand for 18 hours at 25° C. Removal of the solvent in vacuo affords 1.1 g of the title product as a yellow foam. $^1$H-NMR($D_2O$) 1.2 (t, 3H), 1.25–1.5 (m, 2H), 1.65 (p, 2H), 1.8–2.0 (m, 2H), 2.2 (s, 3H), 3.55 (t, 2H), 4.0 (t, 1H), 4.2 (t, 2H).

Elemental Analysis Calcd. for $C_{11}H_{20}N_3O_4Cl_1$+0.5 $H_2O$: C, 43.64; H, 6.99; N, 13.88. Found: C, 43.84; H, 7.22; N, 14.23.

EXAMPLE 4

αS-amino-2,5-dihydro-3-methyl-5-oxo-1,2,4-oxadiazole-2-hexanoic acid, monohydrochloride

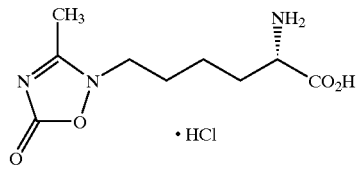

EXAMPLE 4A

N6-hydroxy-N6-(1-iminoethyl)-N2-[(phenylmethoxy)carbonyl]-L-lysine, methyl ester α-Cbz-protected hydroxylysine methyl ester was prepared as described in J. Org. Chem. 59, 4858–4861 (1994). This material is then allowed to react with ethyl acetimidate to afford the hydroxamidine.

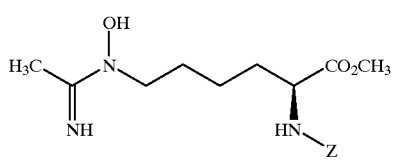

Mass spectrum determined for $C_{17}H_{25}N_3O_5M^+H=352$

EXAMPLE 4B methyl 2,5-dihydro-3-methyl-5-oxo-αS-[[(phenylmethoxy)carbonyl]amino]-1,2,4-oxadiazole-2-hexanoate Reaction with carbonyldiimidazole in methylene chloride affords the cyclized hydroxamidine.

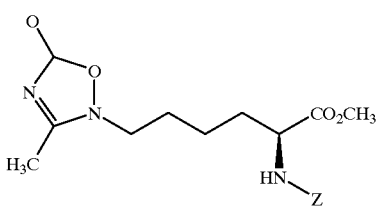

EXAMPLE 4C

Deprotection with HBr in acetic acid affords the title compound.

EXAMPLE 5

αS-amino-4,5-dihydro-3-methyl-5-thioxo-1,2,4-oxadiazole-4-hexanoic acid, monohydrochloride

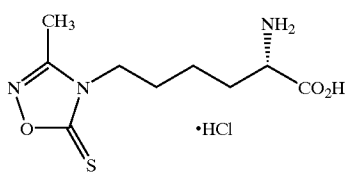

EXAMPLE 5A

αS-[[(1,1-dimethylethoxy)carbonyl]amino]-4,5-dihydro-3-methyl-5-thioxo-1,2,4-oxadiazole-4-hexanoic acid Reaction of the product of EXAMPLE 1A with thiocarbonyldiimidazole followed by DBU affords the cyclized hydroxamidine (J. Med. Chem. 39, 5228–5235 (1996)).

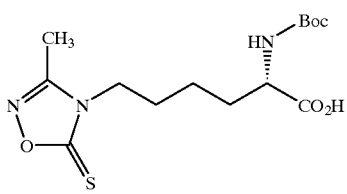

EXAMPLE 5B

Deprotection with Aqueous HCl followed by lyophilization affords the title product.

EXAMPLE 6

αS-amino-4,5-dihydro-3-methyl-5-thioxo-1,2,4-thiadiazole-4-hexanoic acid, monohydrochloride

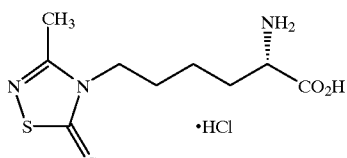

EXAMPLE 7

αS-amino-2,5-dihydro-3-methyl-5-thioxo-1,2,4-oxadiazole-2-hexanoic acid, monohydrochloride

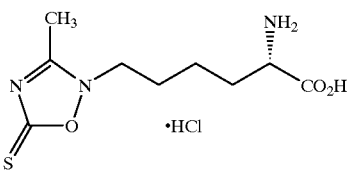

EXAMPLE 7A

N6-hydroxy-N6-(1-iminoethyl)-N2-[(phenylmethoxy)carbonyl]-L-lysine, methyl ester α-Cbz-protected hydroxylysine methyl ester is prepared as described in J. Org. Chem. 59, 4858–4861 (1994). This material is then allowed to react with ethyl acetimidate to afford the hydroxamidine.

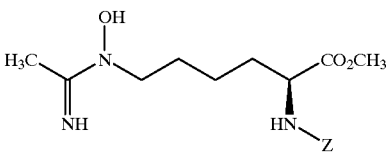

EXAMPLE 7B 2,5-dihydro-3-methyl-αS-[[(phenylmethoxy)carbonyl]amino]-5-thioxo-1,2,4-oxadiazole-2-hexanoic acid Reaction with thiocarbonyldiimidazole followed by DBU affords the cyclized hydroxamidine (J. Med. Chem. 39, 5228–5235 (1996)).

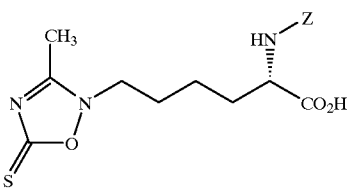

EXAMPLE 7C

Deprotection with HBr in acetic acid affords the title compound.

EXAMPLE 8

αS-amino-4-methyl-5H-1,2,3,5-oxathiadiazole-5-hexanoic acid, 2-oxide, monohydrochloride

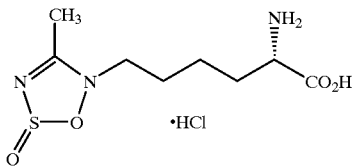

EXAMPLE 8A

N6-hydroxy-N6-(1-iminoethyl)-N2-[(phenylmethoxy)carbonyl]-L-lysine, methyl ester α-Cbz-protected hydroxylysine methyl ester is prepared as described in J. Org. Chem. 59, 4858–4861 (1994). This material is then allowed to react with ethyl acetimidate to afford the hydroxamidine.

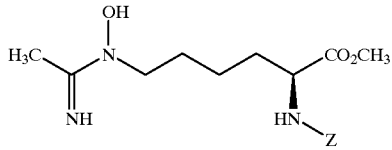

EXAMPLE 8B 4-methyl-αS-[[(phenylmethoxy)carbonyl]amino]-5H-1,2,3,5-oxathiadiazole-5-hexanoic acid, 2-oxide Reaction with thionyl chloride and pyridine affords the cyclized hydroxamidine (J. Med. Chem. 39, 5228–5235 (1996)).

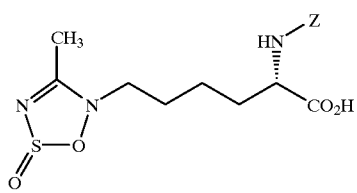

EXAMPLE 8C

Deprotection with HBr in acetic acid affords the title compound.

EXAMPLE 9

αS-amino-4-methyl-3H-1,2,3,5-oxathiadiazole-3-hexanoic acid, 2,2-dioxide, monohydrochloride

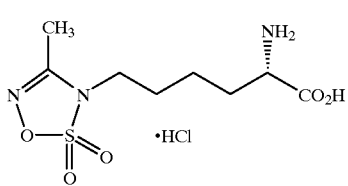

EXAMPLE 9A

αS-[[(1,1-dimethylethoxy)carbonyl]amino]-4-methyl-5H-1,2,3,5-oxathiadiazole-5-hexanoic acid, 2,2-dioxide The product of EXAMPLE 1A is allowed to react with sulfuryl chloride and pyridine to afford the cyclized hydroxamidine.

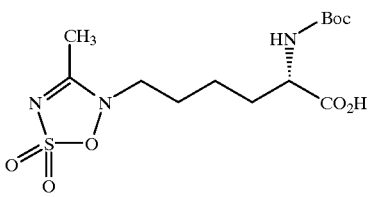

EXAMPLE 9B

Deprotection with aqueous HCl affords the title compound.

EXAMPLE 10

αS-amino-4,5-dihydro-2-methyl-4,5-dioxo-1H-imidazole-1-hexanoic acid, monohydrochloride

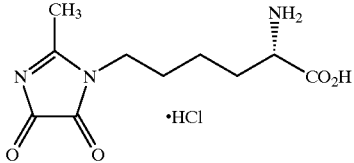

EXAMPLE 10A

N2-[(1,1-dimethylethoxy)carbonyl]-N6-(1-iminoethyl)-L-lysine

A solution of α-Boc-L-lysine in 70 mL of water was adjusted to pH=9.5 by addition of 2.5 N NaOH. Ethyl acetimidate was added portionwise to this solution. After the addition was complete, the solution was allowed to stand at 25° C. for 25 minutes. The solution was then adjusted to pH=7.5 with 1N HCl and poured onto a Dowex 50 Cation exchange column (H$^+$ form. The column was washed with water. The Boc-protected product was then eluted with 10% aqueous pyridine.

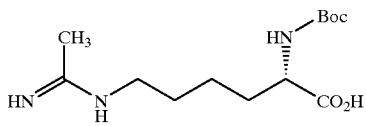

EXAMPLE 10B

αS-[[(1,1-dimethylethoxy)carbonyl]amino]-4,5-dihydro-2-methyl-4,5-dioxo-1H-imidazole-1-hexanoic-acid This product is then allowed to react with oxalyl chloride and pyridine to afford the cyclized amidine.

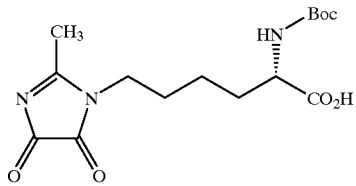

EXAMPLE 10C

Deprotection with aqueous HCl affords the title product.

EXAMPLE 11

αS-amino-5,6-dihydro-3-methyl-5,6-dioxo-4H-1,2,4-oxadiazine-4-hexanoic acid, monohydrochloride

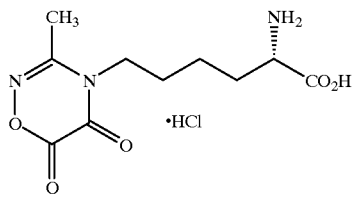

EXAMPLE 11A

αS-[[(1,1-dimethylethoxy)carbonyl]amino]-5,6-dihydro-3-methyl-5,6-dioxo-4H-1,2,4-oxadiazine-4-hexanoic acid The product of EXAMPLE 1A is allowed to react with oxalyl chloride and pyridine to afford the cyclized amidine.

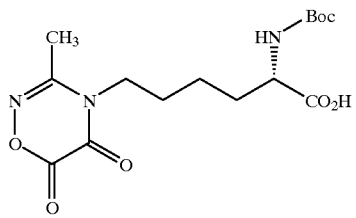

EXAMPLE 11B

Deprotection with aqueous HCl affords the title product.

EXAMPLE 12

αS-amino-5,6-dihydro-3-methyl-5,6-dioxo-2H-1,2,4-oxadiazine-2-hexanoic acid, monohydrochloride

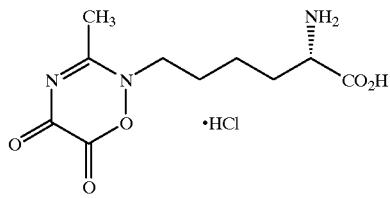

EXAMPLE 12A

N6-(1-iminoethyl)-N2-[(phenylmethoxy)carbonyl]-L-lysine

α-Cbz-protected hydroxylysine methyl ester is prepared as described in J. Org. Chem. 59, 4858–4861 (1994). This material is then allowed to react with ethyl acetimidate to afford the hydroxamidine.

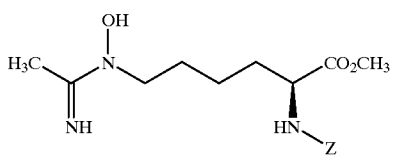

EXAMPLE 12B 5,6-dihydro-3-methyl-5,6-dioxo-αS-[[(phenylmethoxy)carbonyl]amino]-2H-1,2,4-oxadiazine-2-hexanoic acid This hydroxamidine is allowed to react with oxalyl chloride and pyridine to afford the cyclized amidine.

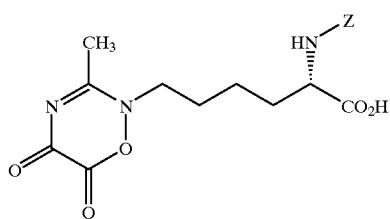

EXAMPLE 12C

Deprotection with HBr in acetic acid affords the title product.

EXAMPLE 13

αS-amino-2,3-dihydro-4-methyl-2,6-dioxo-6H-1,3,5-oxadiazine-3-hexanoic acid, monohydrochloride

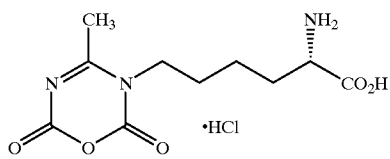

EXAMPLE 14

αS-amino-4-methyl-3H-1,2,3,5-oxathiadiazole-3-hexanoic acid, 2-oxide, monohydrochloride

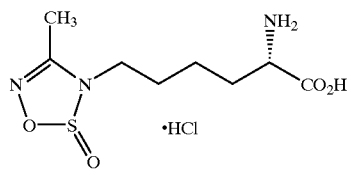

EXAMPLE 14A

αS-[[(1,1-dimethylethoxy)carbonyl]amino]-4-methyl-3H-1,2,3,5-oxathiadiazole-3-hexanoic acid, 2-oxide The product of EXAMPLE 1A is allowed to react with thionyl chloride and pyridine to afford the cyclized hydroxamidine (J. Med. Chem. 39, 5228–5235 (1996)).

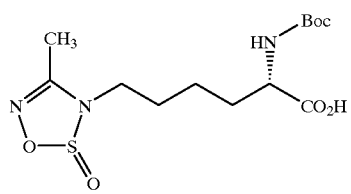

EXAMPLE 14B

Deprotection with aqueous HCl affords the title compound.

EXAMPLE 15

αS-amino-4,5-dihydro-3-methyl-5-oxo-1,2,4-thiadiazole-4-hexanoic acid, monohydrochloride

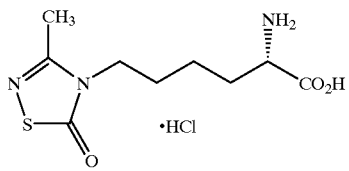

EXAMPLE 15A

αS-[[(1,1-dimethylethoxy)carbonyl]amino]-4,5-dihydro-3-methyl-5-oxo-1,2,4-thiadiazole-4-hexanoic acid The product of EXAMPLE 1A is allowed to react with thiocarbonyldiimidazole followed by $BF_3.OEt_2$ to afford the cyclized hydroxamidine (J. Med. Chem. 39, 5228–5235 (1996)).

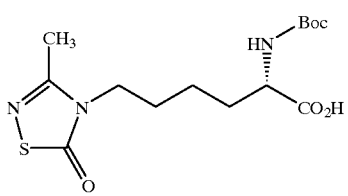

EXAMPLE 15B

Deprotection with aqueous HCl affords the title compound.

EXAMPLE 16

2-amino-6-(4,5-dihydro-3-methyl-5-oxo-1,2,4-oxadiazol-4-yl)-2-hexenoic acid monohydrochloride

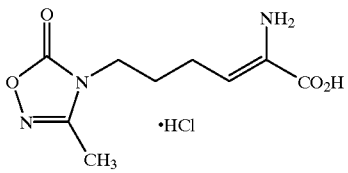

EXAMPLE 16A

N-[4-(phenylmethoxy)butyl]acetamide

Acylation of 1-benzyloxy-4-aminobutane with acetic anhydride affords the 1-benzyloxy, N-[4-(phenylmethoxy)butyl]acetamide.

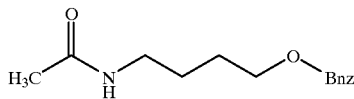

EXAMPLE 16B

N'-hydroxy-N-[4-(phenylmethoxy)butyl]
ethanimidamide monohydrochloride

Formation of the iminoether of the product Example 16A with trimethyloxonium tetrafluoroborate followed by reaction with hydroxylamine hydrochloride affords the hydroxamidine.

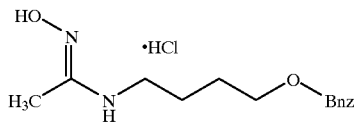

EXAMPLE 16C 4,5-dihydro-3-methyl-4-[4-(phenylmethoxy)butyl]-1,2,4-oxadiazol-5-one The hydroxamidine product of Example 16B is allowed to react with carbonyl diimidazole in methylene chloride in the presence of diisopropylethylamine (DIEA). The reaction mixture is diluted with dilute aqueous HCl and extracted with ethyl acetate. The organic layer is dried (MgSO$_4$), filtered and concentrated to afford the oxadiazol-5-one.

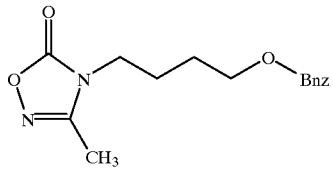

EXAMPLE 16D 4,5-dihydro-3-methyl-4-(4-hydroxybutyl)-1,2,4-oxadiazol-5-one

The product of Example 16C is stirred with hydrobromic acid in acetic acid to afford the alcohol.

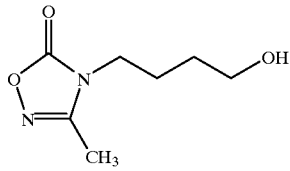

EXAMPLE 16E 4,5-dihydro-3-methyl-5-oxo-1,2,4-oxadiazole-4-butanal

Oxidation of the alcohol product of Example 16D with pyridinium chlorochromate affords the aldehyde.

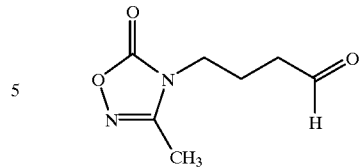

EXAMPLE 16F methyl 6-(4,5-dihydro-3-methyl-5-oxo-1,2,4-oxadiazol-4-yl)2-[[(1,1-dimethylethoxy)carbonyl]amino]-2-hexenoate (±)-Z-α-phosphonoglycine trimethyl ester (Fluka) and 1,8-diazabicyclo[5.4.0]undec-7-ene (DBU) are combined in CH$_2$Cl$_2$. After stirring at room temperature for 30 min, a solution of the aldehyde product of Example 16E in CH$_2$Cl$_2$ is added. The reaction is stirred at room temperature overnight before it is diluted with CH$_2$Cl$_2$. The organic layer is washed with 1 N KHSO$_4$ and brine, dried (Na$_2$SO$_4$), filtered and stripped of all solvent to give the crude title product. This material is purification via flash column chromatography.

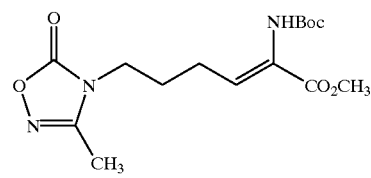

EXAMPLE 16G

Deprotection and hydrolysis of the product of Example 16F in aqueous HCl affords the title product.

Biological Data

The subject compounds of formula (I) have been found to inhibit nitric oxide synthase and posses useful pharmacological properties as demonstrated in one or more of the following assays:

Citrulline Assay for Nitric Oxide Synthase

NOS activity was measured by monitoring the conversion of L-[2,3-$^3$H]-arginine to L-[2,3-$^3$H]-citrulline. Mouse inducible NOS (miNOS) was prepared from an extract of LPS-treated mouse RAW 264.7 cells and rat brain constitutive NOS (rnNOS) was prepared from an extract of rat cerebellum. Both preparations were partially purified by DEAE-Sepharose chromatography. Enzyme (10 μL) was added to 40 μL of 50 mM Tris (pH 7.6) and the reaction initiated by the addition of 50 μL of a solution containing 50 mM Tris (pH 7.6), 2.0 mg/mL bovine serum albumin, 2.0 mM DTT, 4.0 mM CaCl$_2$, 20 μM FAD, 100 μM tetrahydrobiopterin, 2.0 mM NADPH and 60 μM L-arginine containing 0.9 μCi of L-[2,3-$^3$H]-arginine. For constitutive NOS, calmodulin was included at a final concentration of 40 nM. Following incubation at 37° C. for 15 minutes, the reaction was terminated by addition of 300 μL cold buffer containing 10 mM EGTA, 100 mM HEPES (pH 5.5) and 1.0 mM L-citrulline. The [$^3$H]-citrulline was separated by chromatography on Dowex 50W X-8 cation exchange resin and radioactivity quantified with a liquid scintillation counter.

Raw Cell Nitrite Assay

RAW 264.7 cells are plated to confluency on a 96-well tissue culture plate grown overnight (17h) in the presence of LPS to induce NOS. A row of 3–6 wells were left untreated and served as controls for subtraction of nonspecific background. The media was removed from each well and the cells are washed twice with Kreb-Ringers-Hepes (25 mM, pH 7.4) with 2 mg/ml glucose. The cells are then placed on ice and incubated with 50 mL of buffer containing L-arginine (30 mM)+/−inhibitors for 1 h. The assay is initiated by warming the plate to 37° C. in a water bath for 1 h. Production of nitrite by intracellular INOS is linear with time. To terminate the cellular assay, the plate of cells is placed on ice and the nitrite-containing buffer removed and analyzed for nitrite using a previously published fluorescent determination for nitrite. T. P. Misko et al, *Analytical Biochemistry*, 214, 11–16 (1993). All values are the average of triplicate wells and are compared to a background-subtracted induced set of cells (100% value).

In Vivo Assay

Rats were treated with an intraperitoneal injection of 10 mg/kg of endotoxin (LPS) with or without oral administration of the nitric oxide synthase inhibitors. Plasma nitrites were measured 5 hours post-treatment. The results show that the administration of the nitric oxide synthase inhibitor decreases the rise in plasma nitrites, a reliable indicator of the production of nitric oxide, induced be endotoxin.

TABLE I

Human in vitro Enzyme Data

| Compound | hiNOS IC50 [μM] | hecNOS IC50 [μM] | hncNOS IC50 [μM] |
|---|---|---|---|
| Example 1 | >1000 | >1000 | >1000 |
| Example 2 | 138 | 1141 | 159 |
| Example 3 | 124 | 1430 | 200 |

TABLE II

Low Dose LPS*

| | in vivo Effective dose (p.o.) | |
|---|---|---|
| Compound | 3 (mg/kg/day) | 10 (mg/kg/day) |
| Example 2 | 39% inh. | 42% inh. |

*Low Dose LPS refers to the in vivo low-endotoxin assay carried out on mouse as described above.

TABLE III

Low Dose LPS*

| Compound | in vivo Effective Dose (i.v.) 3 (mg/kg/day) |
|---|---|
| Example 2 | 83% inh. |

*Low Dose LPS refers to the in vivo low-endotoxin assay carried out on mouse as described above.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound having the formula;

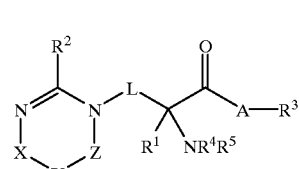

(I)

and pharmaceutically acceptable salts, wherein:
A is O, S, or NR, wherein:
R is selected from the group consisting of hydrogen, lower alkyl, lower alkenyl, lower alkynyl, cycloalkyl, cycloalkenyl, oxathiadiazole, aryl, and alkylaryl, all optionally substituted by one or more of alkyl, hydroxy, alkoxy, halogen, haloalkyl, cyano, amino, and nitro; or
NR together form a heterocyclic;
$R^1$ is selected from the group consisting of hydrogen, lower alkyl, hydroxyalkyl, alkoxyalkyl, haloalkyl, cycloalkyl, oxathiadiazole, aryl, and alkylaryl, all optionally substituted by one or more of alkyl, hydroxy, alkoxy, halogen, haloalkyl, cyano, amino, and nitro;
$R^2$ is selected from the group consisting of amino, thioalkoxy, alkoxy, lower alkyl, lower alkenyl, and lower alkynyl, cycloalkyl, cycloalkenyl, haloalkyl, aryl, oxathiadiazole, alkylaryl, alkoxyalkyl, and thioalkoxyalkyl all optionally substituted by one or more of alkyl, hydroxy, alkoxy, halogen, haloalkyl, cyano, amino, and nitro;
$R^3$ is is selected from the group consisting of H, lower alkyl, lower alkenyl, lower alkynyl, cycloalkyl, cycloalkenyl, aryl, oxathiadiazole, and alkylaryl, all optionally substituted by one or more of halogen, haloalkyl, cyano, nitro, —$CO_2R$, and —COR; or
$R^3$ is selected from the group consisting of alkylhydroxy, alkylpolyhydroxy, alkyl(poly) oxyacyl, $CH_2C(=O)OR^6$, $CH_2C(=O)NHR^6$, $CH_2OC(=O)R^6$, and $CH_2OC(=O)JR^6$, the $CH_2$ is optionally substituted by one or more of lower alkyl, cycloalkyl, oxathiadiazole, aryl, amidino, guanidino, $CO_2H$, amino, hydroxy, thiol, halogen, haloalkyl, cyano, and nitro;
J is selected from the group consisting of O, S, $CH_2$, $CHR^6$, $C(R^6)_2$, NH, and $NR^6$;
$R^4$ is selected from the group consisting of H, $S(O)R^7$, $SO_2R^7$, $CH_2OC(O)$—$R^7$, and $C(O)$—$R^7$ where $C(O)$—$R^7$ represents amino acids or $R^7$ is defined as below, or $R^4$ and $R^3$ taken together comprise a oxathiadiazole, optionally substituted with alkyl or oxygen, or taken together comprise a metal complex containing a divalent cation, or a boron complex;
$R^5$ is $R^6$ or $C(O)$—$R^6$;
$R^6$ is selected from the group consisting of hydrogen, alkyl, alkenyl, alkynyl, cycloalkyl, oxathiadiazole, and aryl, all optionally substituted by one or more alkyl, hydroxy, alkoxy, halogen, trifluoromethyl, nitro, cyano, and amino groups;
$R^7$ is selected from the group consisting of substituted dihydropyridyl, alkyl, thioalkoxy, alkoxy, amino, and cycloalkoxy, all optionally substituted with one or more of amino, alkyl, alkylaryl, oxathiadiazole, and alkylmercaptoalkyl, which may optionally be substituted with one or more of hydroxy, amino, guanidino, and iminoalkyl;

L is selected from the group consisting of lower alkylenes, lower alkenylenes and lower alkynylenes which may optionally be substituted by one or more alkyl, alkoxy, hydroxy, halogen, trifluoromethyl, nitro, cyano, and amino groups; or L is selected from the group consisting of the formula —$(CH_2)_kQ(CH_2)_t$— where k is 1, 2 or 3, t is 1, 2 or 3 and Q is O, Se, $Se(O)_g$, $SiE_2$ where E is lower alkyl, aryl, $S(O)_g$ where g is 0, 1 or 2, or NR; or L is selected from the group consisting of the formula —$(CH_2)_mT(CH_2)_n$— where m is 0, 1 or 2, n is 0, 1 or 2, T is a 3 to 6 membered carbocyclic or oxathiadiazole, or aromatic ring which may optionally be substituted by one or more substituents selected from the group consisting of lower alkyl, lower alkoxy, hydroxy, halogen, nitro, cyano, trifluoroalkyl and amino;

X is selected from the group consisting of O, S(=O), and $SO_2$;

Y is a bond;

Z is selected from the group consisting of O, S(=O), and $SO_2$ with the proviso that one of X or Z is O, and X≠Z.

2. A compound as recited in claim 1 wherein:

A is O, S, or NR, wherein:

R is selected from the group consisting of hydrogen, lower alkyl, lower alkenyl, lower alkynyl, cycloalkyl, cycloalkenyl, oxathiadiazole, aryl, and alkylaryl, all optionally substituted by one or more of alkyl, hydroxy, cyano, amino, and nitro; or NR together form a heterocycle;

$R^1$ is is selected from the group consisting of hydrogen, lower alkyl, hydroxyalkyl, alkoxyalkyl, haloalkyl, cycloalkyl, oxathiadiazol, aryl, and alkylaryl;

$R^2$ is selected from the group consisting of amino, thioalkoxy, alkoxy, lower alkyl, lower alkenyl, lower alkynyl, cycloalkyl, cycloalkenyl, haloalkyl, aryl, oxathiadiazole, alkylaryl, alkylheterocycle, alkoxyalkyl, and thioalkoxyalkyl all optionally substituted by one or more of alkyl, hydroxy, cyano, amino, and nitro;

$R^3$ is selected from the group consisting of H, lower alkyl, lower alkenyl, lower alkynyl, cycloalkyl, cycloalkenyl, aryl, oxathiadiazole, and alkylaryl, all optionally substituted by one or more of cyano, nitro, —$CO_2R$, and —COR; or $R^3$ is selected from the group consisting of $CH_2C(=O)OR^6$, $CH_2C(=O)NHR^6$, $CH_2OC(=O)R^6$, and $CH_2OC(=O)JR^6$, the $CH_2$ is optionally substituted by one or more of lower alkyl, cycloalkyl, oxathiadiazole, aryl, amidino, guanidino, $CO_2H$, amino, hydroxy, thiol, halogen, haloalkyl, cyano, and nitro;

J is selected from the group consisting of O, S, $CH_2$, $CHR^6$, $C(R^6)_2$, NH, and $NR^6$;

$R^4$ is selected from the group consisting of H, $S(O)R^7$, $SO_2R^7$, $CH_2OC(O)$—$R^7$, and $C(O)$—$R^7$ where $C(O)$—$R^7$ represents amino acids or $R^7$ is defined as below, or $R^4$ and $R^3$ taken together comprise a oxathiadiazole;

$R^5$ is $R^6$ or $C(O)$—$R^6$;

$R^6$ is selected from the group consisting of hydrogen, alkyl, alkenyl, alkynyl, cycloalkyl, oxathiadiazole, and aryl all optionally substituted by one or more alkyl, hydroxy, nitro, cyano, or amino groups;

$R^7$ is selected from the group consisting of substituted dihydropyridyl, alkyl, thioalkoxy, alkoxy, amino, and cycloalkoxy, all optionally substituted with one or more of amino, alkyl, alkylaryl, oxathiadiazole, and alkylmercaptoalkyl, which may optionally be substituted with one or more of hydroxy, amino, guanidino, and iminoalkyl;

L is selected from the group consisting of lower alkylenes, lower alkenylenes and lower alkynylenes which may optionally be substituted by one or more alkyl, hydroxy, nitro, cyano, and amino groups; or L is selected from the group consisting of the formula —$(CH_2)_kQ(CH_2)_t$— where k is 1, 2 or 3, t is 1, 2 or 3 and Q is O, Se, $Se(O)_g$, $SiE_2$ where E is lower alkyl, aryl, $S(O)_g$ where g is 0, 1 or 2, or NR; or L is selected from the group consisting of the formula —$(CH_2)_mT(CH_2)_n$— where m is 0, 1 or 2, n is 0, 1 or 2, T is a 3 to 6 membered carbocyclic ring, or aromatic ring which may optionally be substituted by one or more substituents selected from the group consisting of lower alkyl, lower alkoxy, hydroxy, halogen, nitro, cyano, trifluoroalkyl and amino.

3. The compound as recited in claim 2 wherein:

A is O, S, or NR;

R is selected from the group consisting of hydrogen, lower alkyl, lower alkenyl, lower alkynyl, cycloalkyl, cycloalkenyl, oxathiadiazole, aryl, and alkylaryl; or NR together form a heterocycle;

$R^1$ is is hydrogen or lower alkyl;

$R^2$ is selected from the group consisting of amino, thioalkoxy, alkoxy, lower alkyl, lower alkenyl, lower alkynyl, cycloalkyl, cycloalkenyl, haloalkyl, aryl, heterocycle, alkylaryl, alkoxyalkyl, and thioalkoxyalkyl all optionally substituted by one or more of alkyl, hydroxy, cyano, amino, and nitro;

$R^3$ is selected from the group consisting of H, lower alkyl, lower alkenyl, lower alkynyl, cycloalkyl, cycloalkenyl, aryl, oxathiadiazole, and alkylaryl, all optionally substituted by one or more of —$CO_2R$, and —COR; or $R^3$ is selected from the group consisting of $CH_2C(=O)OR^6$, $CH_2C(=O)NHR^6$, $CH_2OC(=O)R^6$, and $CH_2OC(=O)JR^6$, the $CH_2$ is optionally substituted by one or more of lower alkyl, cycloalkyl, oxathiadiazole, aryl, amidino, guanidino, $CO_2H$, amino, hydroxy, thiol, halogen, haloalkyl, cyano, and nitro;

J is O, S, or NH;

$R^4$ is H, $CH_2OC(O)$—$R^7$ or $C(O)$—$R^7$;

$R^5$ is $R^6$ or $C(O)$—$R^6$;

$R^6$ is selected from the group consisting of hydrogen, alkyl, alkenyl, alkynyl, cycloalkyl, heterocycle, and aryl;

$R^7$ is selected from the group consisting of substituted dihydropyridyl, alkyl, thioalkoxy, alkoxy, amino, and cycloalkoxy, all optionally substituted with one or more of amino, alkyl, alkylaryl, heterocycle, alkylheterocycle, and alkylmercaptoalkyl, which may optionally be substituted with one or more of hydroxy, amino, guanidino, and iminoalkyl;

L is selected from the group consisting of lower alkylenes and lower alkenylenes which may optionally be substituted by one or more alkyl, hydroxy, nitro, cyano, and amino groups; or L is selected from the group consisting of the formula —$(CH_2)_kQ(CH_2)_t$— where k is 1, 2 or 3, t is 1, 2 or 3 and Q is O, Se, $Se(O)_g$, $SiE_2$ where E is lower alkyl, aryl, or $S(O)_g$ where g is 0, 1 or 2, or NR; or L is selected from the group consisting of the formula —$(CH_2)_mT(CH_2)_n$— where m is 0, 1 or 2, n is 0, 1 or 2, T is a 3 to 6 membered carbocyclic or heterocyclic ring, or aromatic ring which may optionally be substituted by one or more substituents selected from the group consisting of lower alkyl, lower alkoxy, hydroxy, halogen, nitro, cyano, trifluoroalkyl and amino.

4. The compound as recited in claim 3 wherein:

A is O or NR;

R is selected from the group consisting of oxathiadiazole, aryl, and alkylaryl;

$R^1$ is hydrogen;

$R^2$ is selected from the group consisting of amino, lower, alkyl, lower alkenyl, lower alkynyl, cycloalkyl, cycloalkenyl, haloalkyl, aryl, oxathiadiazole, and alkylaryl, alkoxyalkyl, and thioalkoxyalkyl;

$R^3$ is selected from the group consisting of H, lower alkyl, aryl, oxathiadiazole, and alkylaryl; or $R^3$ is $CH_2C(=O)OR^6$ or $CH_2C(=O)NHR^6$, the $CH_2$ is optionally substituted by one or more of lower alkyl, cycloalkyl, oxathiadiazole, aryl, amidino, guanidino, $CO_2H$, amino, hydroxy, thiol, halogen, haloalkyl, cyano, and nitro;

$R^4$ is H, $CH_2OC(O)$—$R^7$ or $C(O)$—$R^7$;

$R^5$ is $R^6$ or $C(O)$—$R^6$;

$R^6$ is selected from the group consisting of hydrogen, alkyl, heterocyclic, and aryl;

$R^7$ is alkyl, optionally substituted with one or more of amino, alkyl, alkylaryl, oxathiadiazole , alkylmercaptoalkyl, hydroxy, guanidino, and iminoalkyl;

L is selected from the group consisting of lower alkylenes and lower alkenylenes; or L is selected from the group consisting of the formula —$(CH_2)_kQ(CH_2)_t$— where k is 1, 2 or 3, t is 1, 2 or 3 and Q is O, Se, $Se(O)_g$, $SiE_2$ where E is lower alkyl, aryl, $S(O)_g$ where g is 0, 1 or 2, or NR; or L is selected from the group consisting of the formula —$(CH_2)_mT(CH_2)_n$— where m is 0, 1 or 2, n is 0, 1 or 2, T is a 3 to 6 membered carbocyclic ring, or aromatic ring.

5. The compound as recited in claim 4 wherein:

A is O;

$R^1$ is hydrogen;

$R^2$ is lower alkyl;

$R^3$ is selected from the group consisting of hydrogen and lower alkyls of about 1 to 4 carbon atoms;

$R^4$ is hydrogen;

$R^5$ is hydrogen;

L is an alkylene having 3 to 5 carbon atoms.

6. The compound as recited in claim 3 selected from the group consisting of:

αS-amino-4-methyl-5H-1,2,3,5-oxathiadiazole-5-hexanoic acid, 2-oxide, monohydrochloride αS-amino-4-methyl-3H-1,2,3,5-oxathiadiazole-3-hexanoic acid, 2,2-dioxide, monohydrochloride αS-amino4-methyl-3H-1,2,3,5-oxathiadiazole-3-hexanoic acid, 2-oxide, monohydrochloride.

7. A method of inhibiting nitric oxide synthesis in a subject in need of such inhibition by administering a therapeutically effective amount of a compound and pharmaceutically acceptable salts of the compound as recited in claim 1, 2, 3, 4, 5, or 6.

8. A method of selectively inhibiting nitric oxide synthesis produced by inducible NO synthase over nitric oxide produced by the constitutive forms of NO synthase in a subject in need of such selective inhibition by administering a therapeutically effective amount of compound and pharmaceutically acceptable salts of the compound as recited in claim 1, 2, 3, 4, 5, or 6.

9. A method of lowering nitric oxide levels in a subject in need of such by administering a therapeutically effective amount of a compound and pharmaceutically acceptable salts as recited in claim 1, 2, 3, 4, 5 or 6.

10. A pharmaceutical composition comprising a compound as recited in claim 1, 2, 3, 4, 5, or 6 together with one or more pharmaceutically acceptable carriers.

* * * * *